(12) United States Patent
Zhong et al.

(10) Patent No.: US 9,709,469 B2
(45) Date of Patent: Jul. 18, 2017

(54) VALVELESS MICROFLUIDIC DEVICE

(71) Applicant: The Regents of the University of California, Oakland, CA (US)

(72) Inventors: Wenwan Zhong, Riverside, CA (US); Runtao Zhong, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 123 days.

(21) Appl. No.: 13/674,054

(22) Filed: Nov. 11, 2012

(65) Prior Publication Data

US 2014/0030717 A1    Jan. 30, 2014

Related U.S. Application Data

(60) Provisional application No. 61/558,851, filed on Nov. 11, 2011.

(51) Int. Cl.
| | | |
|---|---|---|
| C12Q 1/68 | (2006.01) |
| C12P 19/34 | (2006.01) |
| G01N 1/34 | (2006.01) |
| C12N 15/10 | (2006.01) |
| B01L 3/00 | (2006.01) |
| B01L 7/00 | (2006.01) |

(52) U.S. Cl.
CPC .......... *G01N 1/34* (2013.01); *B01L 3/502761* (2013.01); *B01L 3/502784* (2013.01); *C12N 15/1013* (2013.01); *B01L 7/525* (2013.01); *B01L 2200/0647* (2013.01); *B01L 2200/0673* (2013.01); *B01L 2300/087* (2013.01); *B01L 2300/0816* (2013.01); *B01L 2400/043* (2013.01); *B01L 2400/0487* (2013.01)

(58) Field of Classification Search
None
See application file for complete search history.

(56) References Cited

U.S. PATENT DOCUMENTS

| | | | | |
|---|---|---|---|---|
| 5,536,645 A * | 7/1996 | Jay | ................................. | 435/32 |
| 6,124,138 A * | 9/2000 | Woudenberg | ......... | B01L 3/5027 |
| | | | | 435/287.2 |
| 7,439,014 B2 * | 10/2008 | Pamula | ............... | B01F 13/0071 |
| | | | | 435/4 |
| 8,815,576 B2 * | 8/2014 | Beer | ......................... | 435/287.2 |
| 2010/0068764 A1 * | 3/2010 | Sista | ................. | B01L 3/502761 |
| | | | | 435/79 |
| 2010/0240051 A1 * | 9/2010 | Wang | .................... | C12Q 1/686 |
| | | | | 435/6.11 |
| 2012/0164680 A1 * | 6/2012 | McNaughton et al. | ........ | 435/32 |

* cited by examiner

*Primary Examiner* — Young J Kim
(74) *Attorney, Agent, or Firm* — Gavrilovich, Dodd & Lindsey LLP (57) ABSTRACT

Provided are methods, devices and systems for analyte detection using a microfluidic device.

15 Claims, 10 Drawing Sheets

VALVELESS MICROFLUIDIC DEVICE

CROSS REFERENCE TO RELATED APPLICATIONS

The application claims priority under 35 U.S.C. §119 to U.S. Provisional Application Ser. No. 61/558,851, filed Nov. 11, 2011, the disclosure of which is incorporated herein by reference.

STATEMENT REGARDING FEDERALLY SPONSORED RESEARCH

This invention was made with Government support under Grant No. CHE1057113, awarded by the National Science Foundation. The Government has certain rights in the invention.

TECHNICAL FIELD

Provided are methods and devices for detecting and measuring agents. In particular, the disclosure provides methods and devices useful for detection of measurements of agents using microfluidics.

BACKGROUND

Microfluidics is a field of work that deals with the fluid-based transport of mass, momentum, or energy.

SUMMARY

The disclosure provides a valveless microfluidic system comprising a substrate; a plurality of wells located on the substrate at least one flow channel fluidly connecting each of the wells from an inlet to an outlet, each well preloaded with a desired reagent or buffer and the flow channel filled with a fluid that is immiscible with the desired reagent or buffer. In one embodiment, the fluidic system comprises a plurality of flow channels and a plurality of wells fluidly connected with each flow channel. In another embodiment, a first well of the plurality of wells comprises a magnetic bead comprising an analyte binding molecule. In another embodiment, the analyte binding molecule comprises an oligonucleotide, peptide, polypeptide, antibody or nanoparticle. In yet another embodiment, the system further comprises a magnet for moving the magnetic beads through a fluid channel, the magnet positioned relative to the substrate to provide a magnetic field that manipulates the magnetic bead. In yet another embodiment, each well comprises an aqueous material and each fluid channel comprises an oil. In another embodiment, the system further comprises a computer controller for moving the magnet relative to the substrate.

The disclosure also provides a method of purifying an analyte comprising passing an analyte through the flow channels and the plurality of wells of the microfluidic system described above and herein. In one embodiment, one or more wells of the plurality of wells comprises a purification buffer, wash buffer, lyse buffer or any combination of the foregoing for purification of the analyte. In one embodiment, the magnetic beads or moved through the fluid channels by movement of a magnet adjacent to the microfluidic device. In another embodiment, the method purifies an oligonucleotide.

The disclosure also provides a kit comprising a microfluidic system described above and elsewhere herein, preloaded with a desired combination of buffers or reagents.

The disclosure provides an integrated, droplet-based microfluidic platform for simultaneously processing a plurality of biological samples (e.g., miRNA samples). The disclosure provides a rapid and cost-effective prototyping technique, using thiolene-based optical adhesive, to fabricate microfluidic devices. A simple, but effective, syringe pump-based handling stage can be utilized for automatic or programmed operation of multiple magnetic droplets. The disclosure demonstrates the methods of the disclosure by shows miRNAs can be selectively separated from pre-miRNAs, then efficiently extracted from cell lysate matrix with high quality and eluted into RNase-free water for reliable downstream applications, such as on-chip RT reaction and in-tube real-time qPCR detection. Aside from the feasibility of on-line integration of miRNA SPE and RT(-PCR), the assay was as fast and efficient as, and more economic (~4,000%) and more flexible than the commercial kit. This microfluidic platform is also applicable for other applications, which only involve inexpensive and easily accessible equipment, and employ magnetic droplets for sample preparation and detection.

Various embodiment of the disclosure provide:

Photopolymer-based fabrication process of the microfluidic device is rapid, flexible and cost-effective, making it possible for convenient microdevice prototyping and disposable usage;

Design of the microdevice enables parallel, sample-to-answer nucleic acid analysis of multiple biological samples; higher throughput genetic analysis is possible with larger microchip substrates and more compact design with the same scheme;

The microfluidic device is compatible with regular lab equipment, such as multichannel pipette, syringe pump, PCR machine and image scanner/plate reader, which makes the operation process simple, automatic and applicable for research community;

Use of magnetic silica beads to automatically collect, fractionate, purify, and at last deliver nucleic acid samples to detection wells without intensive human operation, with the magnet fixed on a syringe pump and the chip being moved by the pump at programmed direction and speeds;

Solutions needed for sample purification and elution are pre-stored on the chip as aqueous droplets in mineral oil, minimizing further liquid handling;

Only a few microliters of samples are needed, that decreases the mass detection limit. Nucleic acid materials from a couple tens of cells are detectable.

Nucleic acid amplification is done by putting the device into a thermocycler for RT-PCR. The design is highly feasible for incorporation of an on-chip temperature control unit, and for other signaling strategies being developed in the lab, such as cation exchange for signal amplification. Both are under development in the group;

The final signal is detected by a gel imager and requires no advanced optical instruments, increasing the portability of the device and thus its compatibility with point-of-care testing.

The details of one or more embodiments are set forth in the accompanying drawings and the description below. Other features, objects, and advantages will be apparent from the description and drawings, and from the claims.

BRIEF DESCRIPTION OF THE FIGURES

FIG. 1A-E shows a microfluidic chip of the disclosure, a method of design and fabrication. (A) Shows a layout of the microfluidic chip design, which, in this embodiment, contains four parallel channels (each including seven wells for residing of different aqueous droplets). Exemplary dimensions are listed in the figure. (B) Shows a picture of Master-3# (see FIG. 1C(3)), used for one-step PDMS replication. (C) Shows a schematic flow of a microfluidic chip fabrication: (1) Master-1#, made, in this embodiment, from NOA81 and containing only lower channel structures; (2) Master-2#, punched PDMS substrate that was replicated from Master-1#; (3) Master-3#, molded from Master-2# by one-time curing process; (4) microfluidic chip, with PDMS substrate replicated from Master-3# incorporating pre-formed holes. (D-E) Shows a schematic depiction of a devise/system of the disclosure.

FIG. 2A-B shows parallel handling of multiple superparamagnetic particles (SMP) droplets on a microfluidic chip platform. (A) Picture of syringe pump-based handling stage (1) and lateral view to show relative positions (2). (B) Pictures showing the process of SMP droplets manipulation. Pictures 11)~14) show the process of SMP-1 droplets splitting, collection and retaining. Pictures 21)~24) represent the process of SMP-2 droplets moving from wash wells to elution wells.

FIG. 3A-D shows a scheme of microfluidic chip-based miRNA purification. Prior to use, the microfluidic chip was primed with mineral oil and buffers/reagents at designated wells with multichannel pipette. (A) SMP-1 droplets containing the adsorbed large DNA/RNA molecules was split from the sample droplet and finally collected and trapped in the collection well; (B) A suspension of SMP-2 in ethanol was added into the sample droplet to give a solution of 70% ethanol, facilitating adsorption of small RNAs to the SMP-2; (C) SMP-2 droplets containing the adsorbed small RNAs passed through three W5 buffer droplets, then the adsorbed small RNA molecules were eluted to Sigma water droplets; (D) Reaction pre-mix was added to the eluted sample to perform on-line reaction (such as RT reaction).

FIG. 4A-C shows microfluidic chip-based small RNA selective binding and extraction. In these experiments, mir-191 ($10^8$ copies) was spiked into 0.7 µl of 63 nt oligo (1 µM) or 0.1-2 kb RNA ladder (80 ng/µl), and the CE results can be seen in (A) and (B), respectively. (C) is the real-time RT-qPCR results from eluted and collected miRNAs. CE conditions were the same as in FIG. 7 except that separation field for RNA ladder was 364 V/cm.

FIG. 5A-D shows the performance of a microfluidic chip for miRNA purification. In these experiments, hsa-mir-191 was spiked into 2.5 µl of E. coli cell lysate matrix with copy numbers of $10^5$, $10^6$, $10^7$, $10^8$, and the eluents were amplified by using TaqMan microRNA real-time RT-qPCR method. Pipette collected eluents (2.5µ.) were added to 5 µl of RT pre-mix to perform RT reaction; then 0.67 µl of RT product was mixed with 9.33 µl of PCR pre-mix to run real-time qPCR. Data represent three independent experiments and error bars represent standard deviations. (A) Representative amplification profiles. (B) Calibration curve using the data from (A). Amplification efficiency (101.2%, $R^2$>0.998) was calculated from the copy numbers in PCR and the Ct values. (C) Recovery (20%-30%) of different miRNA input. (D) Reproducibility of interchip- (Ct=17.62±0.31, n=4) and intrachip-(Ct=17.48±0.25, n=4) miRNA SPE was measured by using $10^8$ copies of mir-191 input.

FIG. 6A-B shows microfluidic chip-based miRNA analysis from cell lysate. For microfluidic chip-based method, 2.5 µl of cell lysate (80 cell/µl) was loaded and finally eluted into 0.915 µl of RNase-free water for on-chip RT reaction. Using commercial spin columns, 100 µl of cell lysate was required for sample load and finally eluted into 100 µl of RNase-free water, from which 0.915 µl of eluent was injected into the control well of the microfluidic chip for RT reaction. (A) shows very close Ct values between chip-based and kit-based methods from lysates of two cell lines, Jurkat and 293T; each data was repeated at least three times. (B) Amplification profiles and the calibration curve (R2>0.98) for sensitivity test. Sensitivity of cell numbers was measured by purifying a serial dilutions of 293T cell lysate (200, 40, 8, 1.6 cells input) via microfluidic chip and performing on-line RT reaction and off-line real-time qPCR detection.

FIG. 7A-B shows CE-LIF analysis of 63 nt DNA oligos. CE conditions: separation matrix 5% PVP with 4 M urea and 2×SYBR Gold dye in 1×TBE buffer; capillary 75 µm id with 55/40 cm length; injection 182 V/cm for 15 sec, separation 182 V/cm. Before CE runs, each sample was spiked with a 15 nt oligo as an internal standard (IS). (A) Separation of 63 nt and 15 nt oligos, indicating a detectable 63 nt oligo concentration of 0.25 nM. (B) Calibration curve of 63 nt oligo concentration versus normalized fluorescence intensity, showing good linearity in the concentration range of 0.25 nM to 1 nM.

FIG. 8A-B shows a calibration curve for real-time PCR quantitation. In these experiments, hsa-mir-191 was spiked into 2.5 µl of E. coli cell lysate matrix with a copy number of $10^9$ and the eluent were subjected to RT reaction. Serial 10-fold dilutions of the RT product were used as standards to perform real-time qPCR. Pipette collected eluent (2.5 µl) was added to 5 µl of RT pre-mix to perform RT reaction; then 0.67 µl of diluted RT product was mixed with 9.33 µl of PCR pre-mix to run real-time qPCR. (A) Representative amplification profiles. (B) Calibration curve using the data from (A). Amplification efficiency (102.2%, $R^2$>0.998) was calculated from the copy numbers in PCR and the Ct values.

FIG. 10A-B shows results upon integrating PCR on the microfluidic chip platform. (A) Microfluidic chip-based PCR. In these experiments, 1.5 µl of serial 10-fold dilutions of RT product with copy numbers of $10^3$, $10^4$, $10^5$, $10^6$, $10^7$, was mixed with 6 µl of PCR pre-mix to run thermal cycling (28 cycles) on regular PCR machine. PCR product detection was performed by on-line imaging. Each concentration was repeated once and error bars represent standard deviation. (B) Microfluidic chip-based SPE+ RT-PCR. In these experiments, four samples (two blanks and two cell lysate samples) run on-line SPE+ RT-PCR, and the control wells run on-chip PCR with 3 standard concentrations (copy numbers of $10^4$, $10^5$, $10^6$) used to estimate the concentration range of the target in sample.

DETAILED DESCRIPTION

As used herein and in the appended claims, the singular forms "a," "an," and "the" include plural referents unless the context clearly dictates otherwise. Thus, for example, reference to "an analyte" includes a plurality of such analytes and reference to "the channel" includes reference to one or more channels and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications described herein are provided solely for their disclosure prior to the filing date of the present application. Nothing herein is to be construed as an admission that the inventors are not entitled to antedate such disclosure.

Small regulatory RNA molecules, such as microRNAs (miRNAs) and short interfering RNAs (siRNAs), play an important role in regulation of gene expression in various organisms by binding to the target mRNAs through sequence complementation (Liu et al., Proc. Natl. Acad. Sci., 2004, 101:9740-9744). miRNAs are a class of small (~18-24 nt, nucleotide) non-protein coding RNA molecules cleaved from ~70 nt-long hairpin precursor (pre-miRNA) [Science 2001, 294:853-858], which is enzymatically processed from the long primary transcript (pri-miRNA) (Jinek et al., Nature, 2009, 457:405-412). The regulatory role of miRNAs is conducted by incorporating into an active RNA-induced silencing complex (RISC) and resulting in translational repression or degradation of specific target mRNAs (Bartel et al., Cell, 2004, 116:281-297; Genes Dev 2006, 20:515-524). It's estimated that hundreds of miRNAs are encoded in the human genome, dozens of which have now been shown to regulate a diverse variety of cellular processes, both in normal physiology and in disease. (Lu et al., Nature, 2005, 435:834-838). Expression profiles of miRNAs are thought to contain potential diagnostic and prognostic information for various types of tumors (Calin et al., Nat Rev Cancer, 2006, 6:857-866; Garzon et al., Trends Mol Med 2006, 12:580-587).

Challenges exist for the detection of miRNAs with high specificity, sensitivity and accuracy due to their intrinsic characteristics, such as the extremely small size, highly similar sequences (between both the miRNA family members and the mature and precursor miRNAs, pri-miRNAs and pre-miRNAs), small mass fraction (ca. 0.01%) in the total RNA sample and the largely varied relative expression levels (Bartel, Cell, 2004, 116:281). Different approaches have been developed to detect miRNAs, such as Northern blot analysis with radiolabeled probes (Valoczi et al., Nucleic Acids Res, 32: e175, 2004), microarray-based (Thomson et al., Nat Methods 1:47-53, 2004), and PCR-based methods (Griffiths-Jones et al., Nucleic Acids Res 33:e179, 2005), in situ hybridization (Klosterman et al., Nat Methods 3:27-29, 2006), and high-throughput sequencing (Schulte et al., Nucleic Acids Res 38:5919-5928, 2010). Conventionally, miRNA detections are based on the off-line purified total RNA samples or enriched small RNA fractions with the consumption of large sample/reagent volumes. With the separated procedures of total RNA purification and subsequent miRNA detection, these methods are time- and reagent-consuming, non-continuous and difficult to automate, which makes them not ideal for future miRNA diagnostics.

By virtue of their capabilities of flexible combination and dense integration of functional units, reduction in instrument size and sample/reagent consumption, and enhancement of sensitivity, microfluidic devices have emerged as promising technologies for Lab-on-a-chip genetic analysis. To date, a number of microfluidic systems have been developed to perform nucleic acid purification and detection in stand-alone or integrated format. Among these, magnetic droplet-based microfluidic platforms present special features such as simplicity of fabrication, easiness of operation and flexibility of application. Because the magnetic interaction is unaffected by surface charges, pH, ionic strength or temperature, it is compatible with a wide range of substrate materials and (bio) chemical processes. These valveless/pumpless and interface-free microdevices are low-cost, portable and compatible with point-of-care applications. When using silica superparamagnetic particles (SMPs) for genetic analysis the SMP-droplet itself becomes a droplet actuator and nucleic acid solid-phase extractor, even a real-time thermocycler. Despite the unique properties mentioned above, existing SMP-based microsystems face big challenges when it comes to the parallel manipulation of multiple magnetic droplets, or the processing of complex analytes such as miRNAs, which require additional SMP-binding step to remove large DNA/RNA molecules in samples.

The disclosure provides a multi-well/microchannel-array (M2) chip platform for magnetic droplet-based, parallel miRNA purification and reaction/detection. Furthermore, the disclosure provides a rapid and cost-effective prototyping technique based upon an optical adhesive for one-step replication of PDMS chip.

The disclosure demonstrates that methods, devices and manufacturing methods through a simple and convenient manipulation of multiple SMP droplets on the M2 chip by using a syringe pump-based handling stage. For example, the disclosure demonstrates the selective binding and extraction of miRNAs from 63 nt RNA molecules, and results of the characterization of the M2 chip-based miRNA purification. Furthermore, the disclosure demonstrates the integration of solid-phase extraction (SPE) and RT reaction of has-mir-191 from lysates of two cell lines. From these results, the development of the presented M2 chip platform for high throughput and sample-to-answer analysis and diagnostics of miRNAs from biological samples is clearly demonstrated.

Temperature control elements can be optionally present to control evaporation or condensation of fluid flowing through the fluid flow channel. In one aspect, temperature control element comprises a cooling element that reduces the evaporative capacity of a fluid flowing through the system.

Figure 1A:
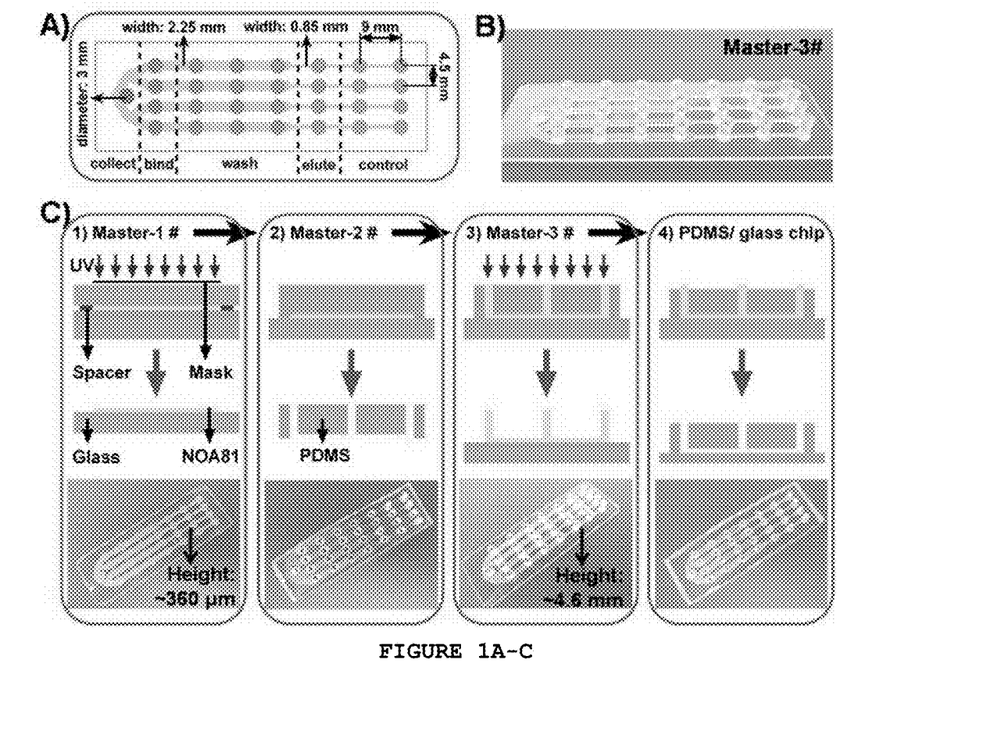
Figure 1D:
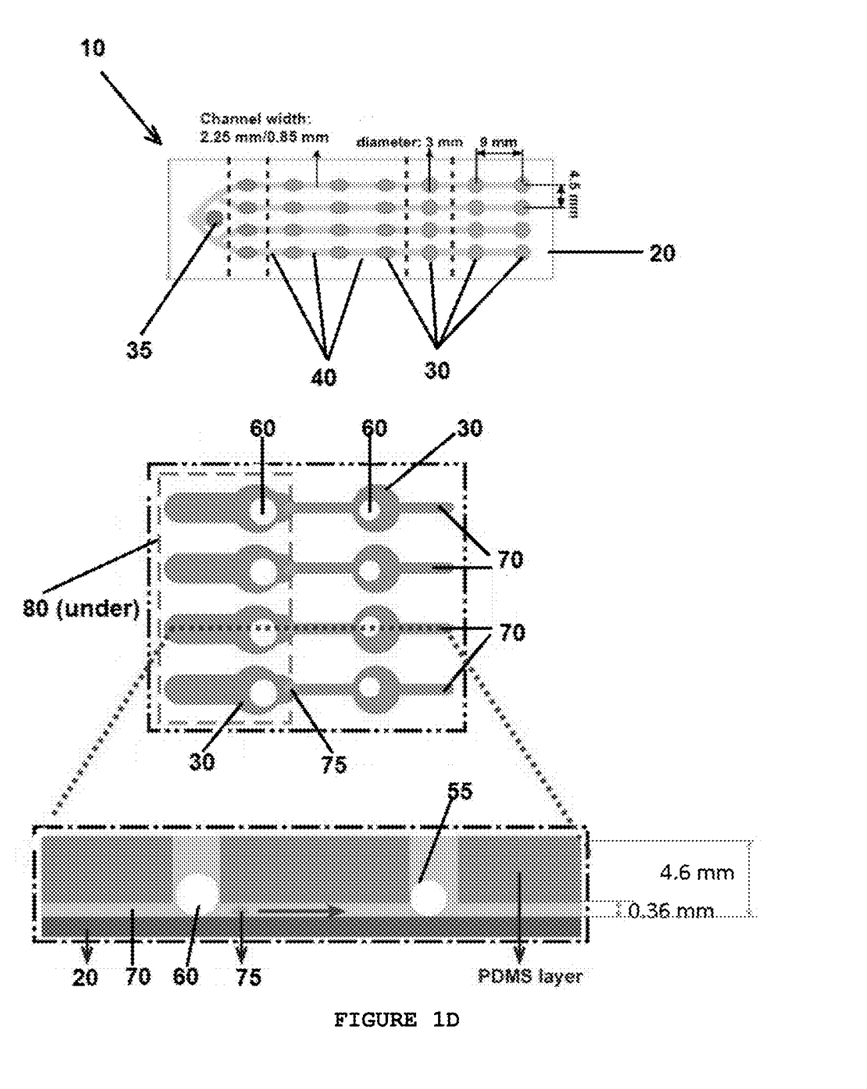

Referring now to FIG. 1D a general diagram of a device and system of the disclosure is provided. Device 10 comprises a substrate 20 and a plurality of wells 30 and a trap well 35 fluidly connected by channels 40. The example depicted in FIG. 1D shows four channels; however, there need only be one channel and the upper limit of channels is only limited by the size of the substrate 20. Accordingly, the number of channels of the device can comprise from 1 to 10 or more (e.g., 1, 2, 3, 4, 5, 6, 7, 8, 9, 10 etc.). Furthermore, FIG. 1D shows 7 wells 30 and a trap well 35. The device and system are not limited by the number of wells so long as there are at least 2. Accordingly, the number of wells may be from 1 to 30 or more (e.g., 1, 2, 3, 4, 5, 6, 7, 8, 9, 10 . . . etc.). The channels and well contain different fluid materials (60 and 70). Typically the fluid materials 60 and 70 are immiscible such as an aqueous fluid and an oil fluid. The wells 30 confine the aqueous droplets 60 with different components and the droplets can be located at the bottom of the well and do not evaporate or disperse into the channels 40 because of the surface tension at the interface of water and oil 55, the friction force of the droplet with the glass surface, and the walls of the wells. The channels 40 comprise an oil 70. The droplets do not flow out of the channel even with gentle agitation. The magnetic beads 75, on the other hand, can be pulled by the magnetic force provided by a magnet 80 located over or under the substrate and come in and out of the aqueous fluid droplets and move between the different fluids in the channels and wells. Because the droplets are physically separated by the wells, they can contain different components for different processing purposes, and their sizes can be tuned depending on the applications. For example, in a small RNA extraction process, after the RNAs on the magnetic beads are cleaned in washing wells, the beads are moved into a narrower channel region and then into a well containing a droplet with a smaller volume. This was the elution droplet. Smaller the volume of the elution solution, higher concentration of the small RNA after eluted, improving sensitivity in detection.

The dimensions of the wells and channels of the device can be varied. With reference to FIG. 1A, certain dimensions are identified, however, these dimensions can be varied depending upon the size of the substrate, the number of wells and channels, the particular use and the types of fluids to be used in the channels and wells.

A variety of working fluids can be used in the systems such as, but not limited to, water (and other aqueous fluids/solutions), silicon oil, mineral oil and glycerol. The fluid selected will be based on the partition coefficient of the analyte to be analyzed. In one embodiment, an aqueous solution is used.

Microfluidic channels 40 can be formed in any number of materials. Thus, the devices of the disclosure include at least one flow channel 40 that allows the passage of an analyte or bead comprising a sample to other channels, wells, components or modules of the system. As will be appreciated by those in the art, the flow channels may be configured in a wide variety of ways, depending on the use of the channel. For example, a single flow channel starting at a sample inlet port may be separated into a variety of smaller channels, such that the original sample is divided into discrete subsamples for parallel processing or analysis. Alternatively, several flow channels from different modules, for example, the sample inlet port and a reagent storage module (e.g., a nanoparticle storage module) may feed together (i.e., converge). As will be appreciated by those in the art, there are a large number of possible configurations; what is important is that the flow channels allow the movement of sample and reagents from one part of the device to another. For example, the path lengths of the flow channels may be altered as needed; for example, when mixing and timed reactions are required, longer flow channels can be used.

In one embodiment, the devices of the disclosure include at least one inlet port for the introduction of a sample to the device. This may be part of or separate from a sample introduction or a sample mixing chamber.

In another aspect of the disclosure, the devices of the disclosure may include a manipulation chamber/well that allows for the mixing of probes and a fluid sample. Optionally, an aggregation stimulant (such as a salt) can be mixed in the manipulation chamber.

In addition to individual straight channels, a functional microfluidic circuit often consists of channel junctions. The positioning of liquid flow at channel junctions can include valve systems.

A fluid device of the disclosure comprises a substrate (which may be one or more substrates associated with one another to define fluid channels there between). The fluid device can comprises a sample inlet in fluid communication with sample fluid flow channel and buffer inlet in fluid communication with buffer fluid flow channel.

In one embodiment, substrate comprises an insulating (e.g. glass or polymer), or a semiconducting (e.g. silicon structures) in which various features (e.g., channels, chambers, valves and the like) are designed. Such features can be made by forming those features into a surface and/or a subsurface structure of substrate using microfabrication techniques known to those skilled in the art.

By extending the above channels and adding more sorting regions downstream, the disclosure provides sorting devices with multi-stage purification. In one aspect, the disclosure provides methods and systems that utilize massive parallelism and multistaging. This allows full utilization of the central benefits of microfabrication technology to achieve high throughput, purity and recovery simultaneously.

Microfabrication technologies provide the ability to implement multiple staging and massive parallelism on a single chip, thus allowing for the production of inexpensive, disposable, flexible, and portable devices.

The devices, systems, methods and techniques can be used to measure any number of agents in any number of industrial applications. The devices, systems and method of the disclosure offer ease of use, speed, and identification of analytes in a portable, relatively inexpensive implementation. Thus, a wide variety of analytes can be identified and analyzed by the disclosed devices, methods and systems. Detectable analyte include broad ranges of chemical classes such as organics including, for example, alkanes; alkenes; alkynes; dienes; alicyclic hydrocarbons; arenes; alcohols; ethers; ketones; aldehydes; carbonyls; carbanions; sugars; biogenic amines; thiols; polynuclear aromatics and derivatives of such organics, e.g., halide derivatives, and the like; biomolecules such as proteins, DNA, RNA, hormones, other signaling components of the endocrine and other biosystems, components of biotissues, blood, and other biofluids; isoprenes and isoprenoids; and fatty acids and derivatives. Accordingly, commercial applications include environmental toxicology and remediation, biomedicine, materials quality control, food (and beverage) and agricultural products monitoring, the presence of wine freshness or bottling, cork or barrel contamination (by contaminants such as 2,4,6-trichloroanisole (TCA) guaiacol, geosmin, 2-methylisoborneol (MIB), octen-3-ol and octen-3-onein), measuring cadaverine for rapid assessment of bacterial quality and/or food spoilage, anaesthetic detection, automobile oil, gasoline, fuel or radiator fluid monitoring, breath alcohol and drug analyzers, hazardous spill identification, explosives detection, biowarfare detection, fugitive emission identification, medical diagnostics, glucose monitoring, fish freshness, detection and classification of bacteria and microorganisms for biomedical uses and medical diagnostic uses, and the like. A wide variety of commercial applications are available including, but not limited to, heavy industrial manufacturing, ambient air monitoring, worker protection, emissions control, product quality testing, leak detection and identification, oil/gas petrochemical applications, combustible gas detection, $H_2S$ monitoring, hazardous leak detection and identification, emergency response and law enforcement applications, illegal substance detection and identification, arson investigation, enclosed space surveying, utility and power applications, emissions monitoring, transformer fault detection, food/beverage/agriculture applications, freshness detection, fruit ripening control, fermentation process monitoring and control applications, flavor composition and identification, product quality and identification, refrigerant and fumigant detection, cosmetic/perfume/fragrance formulation, product quality testing, personal identification, chemical/plastics/pharmaceutical applications, leak detection, solvent recovery effectiveness, perimeter monitoring, product quality testing, hazardous waste site applications, fugitive emission detection and identification, leak detection and identification, perimeter monitoring, transportation, hazardous spill monitoring, refueling operations, shipping container inspection, diesel/gasoline/aviation fuel identification, building/residential natural gas detection, formaldehyde detection, smoke detection, fire detection, automatic ventilation control applications (cooking, smoking, etc.), air intake monitoring, hospital/medical anesthesia and sterilization gas detection, infectious disease detection and breath applications, body fluids analysis, pharmaceutical applications, drug discovery and telesurgery. Another application for the fluidic device of the disclosure is in engine fluid monitoring (e.g., an oil/antifreeze monitor, engine diagnostics for air/fuel optimization, diesel fuel quality and the like). Volatile organic carbon measurement (VOC), fugitive gases in refineries, halitosis, soil and water contaminants, leak detection, fire safety, chemical weapons identification, use by hazardous material teams, explosive detection, breathalyzers, ethylene oxide detectors and anesthetic measurements can also be performed.

The methods and devices of the disclosure can be used for military and public safety in a variety of venues.

In other embodiments, the fluid channels and reservoirs/wells are coated to inhibit the accumulation of biological material (e.g., proteinaceous agents) on the surface. In some embodiments, polyethyleneglycol (PEG) is immobilized on surfaces to prevent nonspecific interactions.

For example, when the analyte is a single-stranded nucleic acid, the binding/targeting ligand (e.g., a magnetic bead) comprises a substantially complementary nucleic acid. Similarly the analyte may be a nucleic acid binding protein and the capture binding ligand is either a single-stranded or double-stranded nucleic acid; alternatively, the binding ligand may be a nucleic acid binding protein when the analyte is a single or double-stranded nucleic acid. When the analyte is a protein, the binding ligands include proteins or small molecules. For example, when the analyte is an enzyme, suitable binding ligands include substrates, inhibitors, and other proteins that bind the enzyme, i.e. components of a multi-enzyme (or protein) complex. As will be appreciated by those in the art, any two molecules that will associate, may be used, either as the analyte or the functional group (e.g., targeting/binding ligand). Suitable analyte/binding ligand pairs include, but are not limited to, antibodies/antigens, receptors/ligand, proteins/nucleic acids; nucleic acids/nucleic acids, enzymes/substrates and/or inhibitors, carbohydrates (including glycoproteins and glycolipids)/lectins, carbohydrates and other binding partners, proteins/proteins; and protein/small molecules. In one embodiment, the binding ligands are portions (e.g., the extracellular portions) of cell surface receptors.

As mentioned above, the detection devices of the disclosure are capable of multi-channel analysis and scaling. The small length scales associated with microfluidics facilitates fabrication of multi-channel devices, whereby each fluid flow channel is sensitive to one, or a class of target analytes.

Multiple microfluidic channels provide flexible designs for 'lab on a chip' concepts. For example, microfluidic channels can be used to provide controlled dilution of analyte. The diluted analyte can then be introduced to nano-particle flow and SERS detection can be performed. The SERS intensity can then be compared to the degree of dilution, to facilitate the deduction of initial analyte concentration.

In one embodiment, magnetic beads are used to move an analyte through the channels and wells. The magnetic beads can be moved by using a magnet located above or below the fluid channels. The magnet is moved relative to the substrate such that the magnetic field causes the magnetic beads to move through the channels and the magnet is moved from one end of the substrate to the other. The movement of the magnet or the substrate relative to the magnet can be controlled by a computer to move at a desired rate or to stop at particular location in the microfluidic chip (e.g., stopping at wells for mixing of the bead with the desired aqueous solution).

In some embodiments, the disclosure provides kits and systems for use in monitoring the level of an analyte in a sample. In some embodiments, the kits are for home use by a subject to assist in identifying an analyte, disease or disorder or to monitor a biological condition.

As used herein, the term "sample" is used in its broadest sense. For example, a sample can comprise a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. The nanostructures can be used, for example, in bodily fluids in vivo or in vitro. Such bodily fluids include, but are not limited to, blood, serum, lymph, cerebral spinal fluid, aqueous humor, interstitial fluid, and urine.

The working examples below are provided to illustrate, not limit, the disclosure. Various parameters of the scientific methods employed in these examples are described in detail below and provide guidance for practicing the disclosure in general.

EXAMPLES

M2 Chip Fabrication.

Figure 1E:
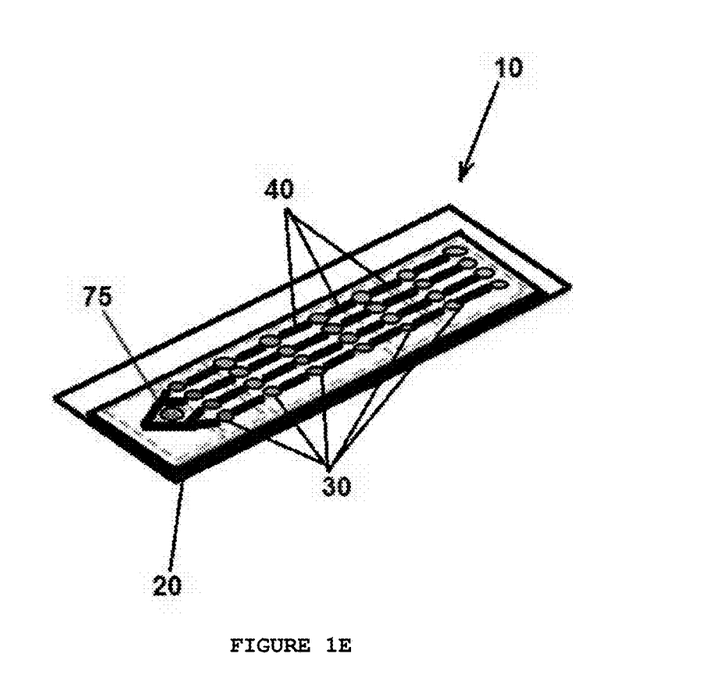

The M2 chip as generally shows in FIG. 1 was made by bonding of a 3"×1" glass slide (0.1 mm-thick) and a cured PDMS substrate, which was replicated from a thiolene-based optical adhesive (NOA81, Norland Products, N.J.) molding master (Master-3#). FIG. 1 shows an M2 chip layout (A) and Master-3# picture (B), as well as schematic flow of the fabrication process (C). Exemplary dimensions are listed in the figure. Firstly, Master-1#, containing only lower channel features made of NOA81 (FIG. 1C-1), was fabricated by using an open-faced method (J. Micromech. Microeng. 14 (2004) 153-158). Briefly, NOA81 was pre-cured with well-defined spacers (~360 µm) placed between a glass slide (plasma treated) and PDMS working stage under collimated UV light source (365 nm, ~8.3 mW/cm$^2$) through a photomask for 5 seconds. After limited exposure, the glass slide was slowly removed from the PDMS slab and a syringe is used to wash out the unexposed adhesive regions by injecting with ethanol, ethanol/acetone mixture (1:1) and ethanol again. The air-dried glass slide was post-cured by flood exposure under UV light for 345 sec to increase the adhesion to glass, followed by a 12 h thermal cure at 50° C. to extend the structure's lifetime. Thereafter, the Master-1# was treated by vapor deposition (dimethyl dichlorosilane) and utilized to mold PDMS (Sylgard 184, Dow Corning, with a 10:1 mass ratio of base to curing agent). The PDMS substrate was cured at 75° C. for 4 hours and peeled off; 3-mm holes were punched with a 9 mm pitch between centers to form Master-2# (FIG. 1C-2). After attaching PDMS Master-2# on a plasma-treated glass slide, NOA81 was injected into the channels and wells without bubble trapping, cured under adequate UV exposure dose (1300 sec) and thermally aged at 50° C. for 12 hours. By carefully removing Master-2#, the final Master-3#, including both lower channel features (~360 µm) and higher pillar structures (~4.6 mm), was accomplished (FIG. 1C-3) and can then be used for replication of PDMS substrate with pre-formed holes (FIG. 1C-4).

Magnetic Droplet Manipulation.

Figure 2A:
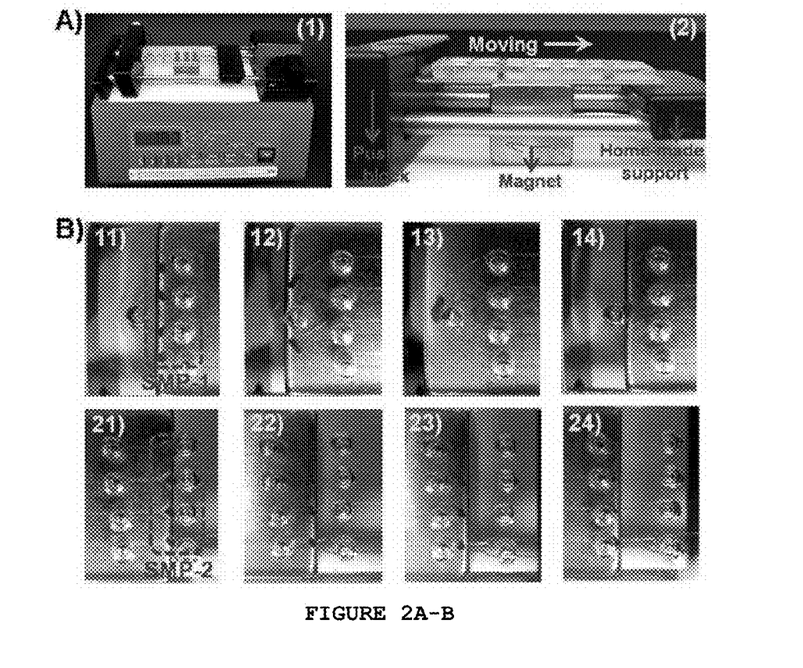

A syringe pump (Model: NE-300, New Era Pump Systems Inc.) based handling stage was used to perform M2 chip-based automatic manipulation of multiple magnetic droplets (FIG. 2A). Prior to use, the M2 chip was treated with silanizing agent and then loaded with M5904 mineral oil (Sigma) and buffers/reagents at designated wells with multichannel pipette. A permanent neodymium magnet (1" cube) was fixed between two guide rods of the syringe pump. The primed M2 chip was put on top of the magnet, attached on the pusher block of the syringe pump by using adhesive tape and held up on the right side by a home-made plastic support, which was assembled on the guide rods. With the pusher block moving from left to right at a velocity of ~1 mm/sec, the M2 chip moves as well, but the SMPs (1 μm diameter) in microwells (submerged in mineral oil) are retained and collected at the edge area of the magnet because of the large gradient of the magnetic field there, causing relative movement of SMPs to M2 chip from right to left. FIG. 2B shows the process of M2 chip-based SMPs manipulation. Pictures 11~14 show the process of separating and retaining SMPs from aqueous droplets. Four small droplets containing SMP (SMP-1) were split from parent droplets (with red dye), merged with each other and finally trapped in the collection well. Pictures 21~24 represent the process of SMP-2 passing through a tapered channel (video-2 in ESI†), moved from wash well (water droplet) to elution well (droplet with blue dye).

MicroRNA Purification.

MicroRNA purification from biological samples is based on the fact that small RNA molecules (including miRNAs) will selectively bind to silica surfaces in the presence of 70% ethanol and a chaotropic salt (User manual for PureLink miRNA Isolation Kit, Invitrogen). Lysis/binding buffer (L3) and washing buffer (W5) was used from a commercial kit (PureLink miRNA Isolation Kit, Invitrogen) to obtain cell lysis and miRNA purification. Cultured cell pellets were resuspended in L3 buffer and mixed well by vortexing. The cell lysate or miRNA sample was diluted using L3 buffer to a proper concentration as a load sample. Prior to injection into the M2 chip, the SMPs were washed twice with nuclease-free water from Sigma-Aldrich (St. Louis, Mo.) and then resuspended in ethanol (>95%) to a specific concentration according to the application.

Figure 3A:
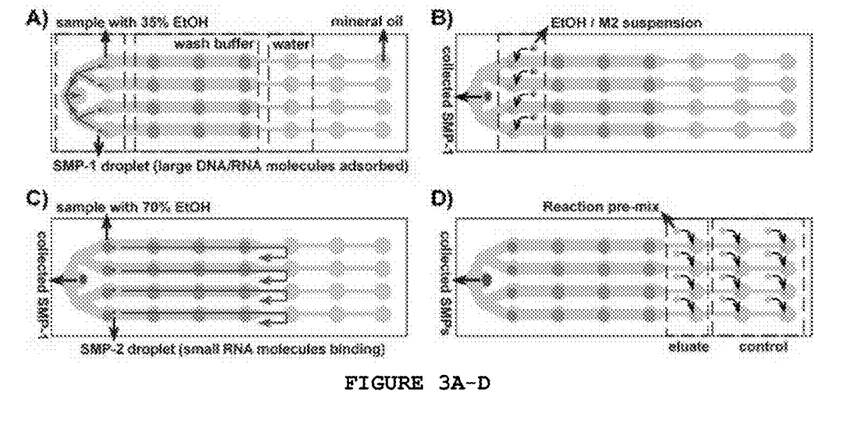

For the miRNA extraction, a suspension (1.35 μL) of SMPs (SMP-1, 100-140 ug) in ethanol was added into a sample droplet (2.5 μL) in the binding well to obtain a solution of 35% ethanol. This solution was further mixed by pipetting up and down 10 times and was then incubated for 4 min. Large nucleic acid molecules adsorbed to the SMP-1 surface while small RNA molecules remained in the solution. Thereafter, a small droplet containing the SMP-1 with the adsorbed large DNA/RNA molecules was split from the sample droplet and finally collected and trapped in the collection well (FIG. 3A). To facilitate the selective binding of small RNA molecules to SMPs, another suspension (4.5 μL) of SMP-2 (60-80 μg) in ethanol was added into the sample droplet to give a solution of 70% ethanol (FIG. 3B). Small RNA molecules bound to the SMP-2 and impurities were diluted and washed away by passing the splitted SMP-2 droplet through three W5 buffer droplets (10 μL, 30 sec each) successively. Finally, the adsorbed small RNA molecules were eluted to a Sigma water droplet (2.5 μL for in-tube RT-qPCR or 0.915 μL for on-chip RT reaction) in elution well. The small RNA-desorbed SMP-2 droplet was removed from the elution well and moved to the collection well (FIG. 3C) in the end. The total miRNA purification process, from the sample injection to elution, takes less than 15 min.

As a comparison, a silica-membrane spin column-based miRNA isolation kit (PureLink, Invitrogen) was run in parallel with the M2 chip for miRNA purification from cell lysate. 100 μL of cell lysate sample diluted in L3 buffer was loaded into the spin column and the purified small RNAs was eluted to 100 μL of Sigma water.

MicroRNA RT-qPCR Detection.

TaqMan microRNA RT kit (Cat. No. 4366596) and primers (Cat. No. 4427975) were purchased for hsa-mir-191 from Ambion (Austin, Tex.). Taq 5× Master Mix for PCR was from New England BioLabs (Cat. No. M0285S). For off-chip real time RT-PCR, 7.5 μL of RT reaction mixture contained 2.5 μL of purified miRNA and 5 μL of RT pre-mix including 1×RT Buffer, 1 mM of dNTP mixture, 25 U of Multiscribe RT enzyme, 2 U of RNase Inhibitor and 1.5 μL of 5×RT stem-loop primers. RT reaction was performed at 16° C. for 30 min, 42° C. for 30 min and 85° C. for 5 min. Thereafter, 0.67 μL of RT product was added into 9.33 μL of PCR pre-mix, containing 2 μL of Taq 5× Master Mix, 0.5 μL of 20× TaqMan probe and primers. The reaction was run on the BioRad CFX96 real-time PCR detection system at 95° C. for 3 min, followed by 45 cycles (95° C. for 15 s and 60° C. for 1 min).

As for on-chip reactions, 0.585 μL of RT pre-mix was added to the elution buffer droplet (0.915 μL) after elution process. Following on-chip RT reactions, the RT product was mixed with 6 μL of PCR pre-mix (including 0.1% bovine serum albumin, BSA to prevent possible enzyme adsorption and improve PCR efficiency) off-chip or on-chip, to perform either real-time PCR for cell lysate analysis or chip-PCR and end-point detection to test the potential of on-chip integration of SPE and RT-PCR. Temperature control was realized by using a regular PCR machine with a 0.4 mm-thick brass plate placed under the M2 chip to enhance heat transfer and temperature uniformity. Mineral oil and small pieces of PDMS spacer was applied to ensure fully thermal contact of the M2 chip to the heating plate. To adjust the set temperatures and durations of the thermal cycler to fit the actual temperature profiles in the droplets, a 0.076 mm-diameter T-type thermocouple (5SC-TT-T-40-36, OMEGA) was inserted into the center of the reaction well. M2 chip fluorescence images were taken by using a Typhoon Image Scanner (GE healthcare) with the following settings: 488 nm laser excitation, 530SP emission filter, 530V PMT gain and normal sensitivity. Image processing was done by using ImageQuant (GE healthcare) or ImageJ (NIH) software.

Capillary Electrophoresis (CE) Analysis.

A home-built CE system equipped with a 488 nm laser (Lei R., Anal. Chem. 2009, 81, 5510-5516) was used for the separation and detection of miRNA and size markers. An established CE condition (Ni L., Anal. Chem. 2009, 81, 4906-4913) was utilized with some modifications: separation matrix 5% Polyvinylpyrrolidone (PVP, average Mw 1,300,000; from Fisher Scientific) with 4 M urea and 2×SYBR Gold dye (Invitrogen) in 1×TBE buffer. Prior to use, the 55 cm fused-silica capillary (75 μm i.d., 365 μm o.d., Polymicro Technologies, Phoenix, Ariz.) with an effective length of 40 cm was rinsed sequentially with 0.1 M HCl, deionized water, methanol, and the sieving matrix using syringes and a hand pump. Before CE runs, each sample was spiked with a 15 nt DNA oligo as an internal standard (IS).

Sample injection was carried out at −10 kV for 15 s, and the separation voltage was −10 kV.

The target miRNA, 15 nt and 63 nt oligos (consisted of only A, C and G bases, used as internal standard and size marker, respectively) were from Integrated DNA Technologies (Coralville, Iowa). The 0.1-2 kb RNA ladder was purchased from Invitrogen (Carlsbad, Calif.). The target strand, hsa-mir-191 was identified as a potential target for Hepatocellular Carcinoma (HCC) therapy and was found to be a regulator of a variety of cancer-related pathways. This miRNA was found to be highly consistent in its expression across 13 normal tissues and five pair of distinct tumor/normal adjacent tissues and was statistically superior to the most commonly used reference RNAs used in miRNA qRT-PCR experiments.

Rapid Prototyping of M2 Chip.

The M2 chip was designed to process multiple samples simultaneously. In this work, the chip contained four parallel channels, each including seven wells for loading of different aqueous droplets (FIG. 1A), enabling purification and reaction of four miRNA samples in parallel. By using regular PDMS molding method to fabricate the PDMS/glass chip, 29 holes needed to be punched each time after PDMS replication, which was tedious and difficult to ensure the consistency of the hole positions and shapes. To simplify and speed up the fabrication process, a rapid prototyping technique was used to make the molding master for convenient PDMS replication with an inexpensive, UV-curable adhesive, NOA 81. This thiolene-based optical adhesive functions as a negative resist in conventional lithography with faster curing rate (down to seconds) and higher feature structures (up to millimeters, see FIG. 1B). After curing, it has very good adhesion to glass, but does not bind to cured PDMS (due to the oxygen dissolved in PDMS that inhibits NOA81 polymerization) [Lab Chip, 2008, 8, 492-494], which enables the open-faced methodology (FIG. 1C-1) [J. Micromech. Microeng. 14 (2004) 153-158] and is fully compatible with PDMS replication techniques. It was feasible to use NOA81 to mold PDMS substrate (FIG. 1C-2) or to be molded by PDMS master (FIG. 1C-3). The three-dimensional Master-3# (containing 360 μm-height channels and 4.6 mm-height pillars) was formed by one time UV exposure (FIG. 1C-3) and was utilized to make consistent M2 chip by one-step PDMS replication (FIG. 1C-4); no further punching procedure was required. Fabrication of such high structures by conventional lithography would be both challenging and time consuming, requiring expensive masks or deep etching techniques. To control the height of the PDMS on Master-3#, a certain amount of PDMS pre-polymer was used, or a negative pressure was employed to remove the extra PDMS. The Master-3# was mechanically stable and reusable, thus reducing the fabrication cost and turnaround.

Parallel Handling of Multiple SMP Droplets.

The M2 chip was designed to operate using only regular laboratory equipment (such as pipettes, magnet, syringe pump and PCR machine), without the need for any kind of microvalves/pumps or external connections. The presented M2 chip consisted of four parallel sample processing units and a SMP-trapping structure (FIG. 1A). Each processing unit included seven wells in a linear configuration connected by microchannels with different widths, and can be used to complete the whole process of miRNA purification and reaction. The seven wells in one unit, for residing different aqueous droplets, were arranged according to the pattern of the standardized 96-well microtiter plates, ensuring compatibility with existing high-throughput laboratory infrastructure (e.g. multichannel pipettes, liquid handling robots, PCR machine). Parallel units can be simultaneously processed by moving the M2 chip using a syringe pump with a magnet underneath the microchip holding the SMPs at the edge area of the magnet (FIG. 2A), enabling simultaneous purification of four miRNA samples. It was easy and convenient to assemble and operate the syringe pump-based handling stage. An automatic purification protocol could be obtained by programming the direction and speed of the pump.

Upon M2 chip priming with mineral oil and reagents, all the droplets were submerged inside the oil, and the whole process was carried out in an oil medium, making the SMP droplet movement easier due to the shorter contact line, and thus the decreased friction between the droplet and the surface. Moreover, a thick layer of mineral oil functioned as a good evaporation barrier during operation. By moving the M2 chip with the syringe pump, different droplets in each processing unit were confined within interconnected wells because of high surface tension and friction. The SMPs, on the other hand, were pulled by the magnetic force and retained at the area of large magnetic field gradient. As a result, the large droplet containing the SMPs elongated, forming regions with and without SMPs. In the end, a small droplet containing SMPs was split from the parent droplet (FIG. 2B) and moved towards the neighboring droplet, finally merged with it, triggering dilution of impurities adsorbed on the SMPs. The wide channels between the sample well and the wash wells facilitated the handling of SMPs, while the narrow channels connecting the wash well and elution well enabled a small critical volume (~0.8 μL), making it possible to incorporate miRNA two-step RT-PCR with SPE on M2 chip.

Small RNA selective binding and extraction. For miRNA purification, it is extremely important to enrich small RNA molecules, such as microRNAs (miRNAs) and short interfering RNAs (siRNAs), in a separate fraction and remove larger RNA and genomic DNA molecules to minimize background on downstream applications. Currently, commercial kits usually employ two-spin column process to purify small RNA species from biological samples and only allow the separation of small RNAs from >200 nt RNAs. The disclosure demonstrates the separation and extraction of small RNAs from precursor miRNA (pre-miRNA, ~70 nt) and other ≥63 nt RNA molecules using the M2 chip-based protocol. The method is based on the selective binding of RNA molecules of different sizes to the SMPs when different ethanol concentrations are present in the binding solution: under low ethanol concentration (35%), large DNA/RNA molecules preferentially bind to the SMPs; at high ethanol concentration (70%), small RNAs can efficiently bind to the SMPs. Incorporating a SMP-trapping structure in the chip design (FIG. 1A), a magnetic droplet based, two-binding SPE procedure was used to perform on-chip miRNA purification (see Materials and Methods Section and FIG. 3). The integrated SMP-trapping structure was used to collect the waste SMP-1 and separate the SMP-1 and SMP-2 to prevent the interference with each other during operation. If desired, the large DNA/RNA species adsorbed on SMP-1 can also be eluted and analyzed.

Figure 4A:
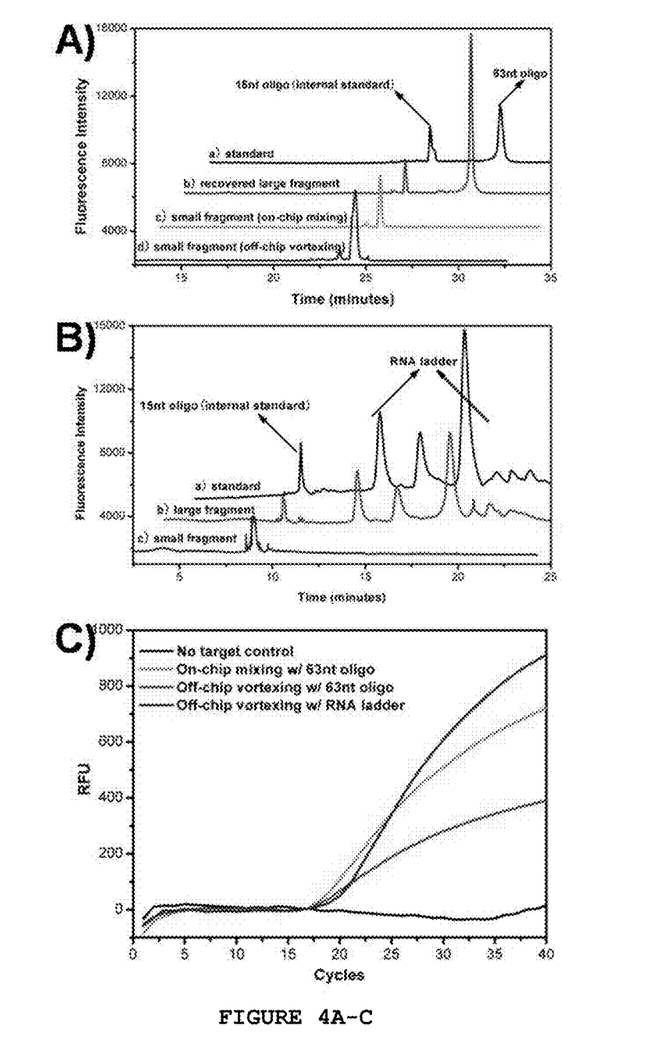
Figure 7A:
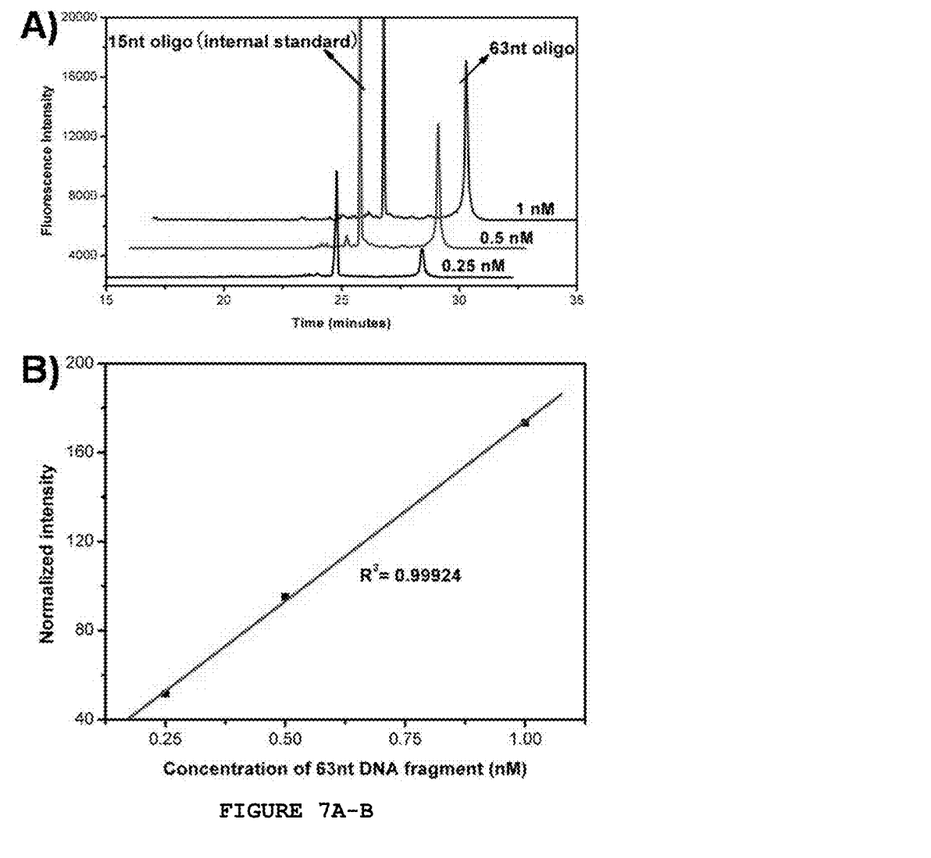
Figure 8A:
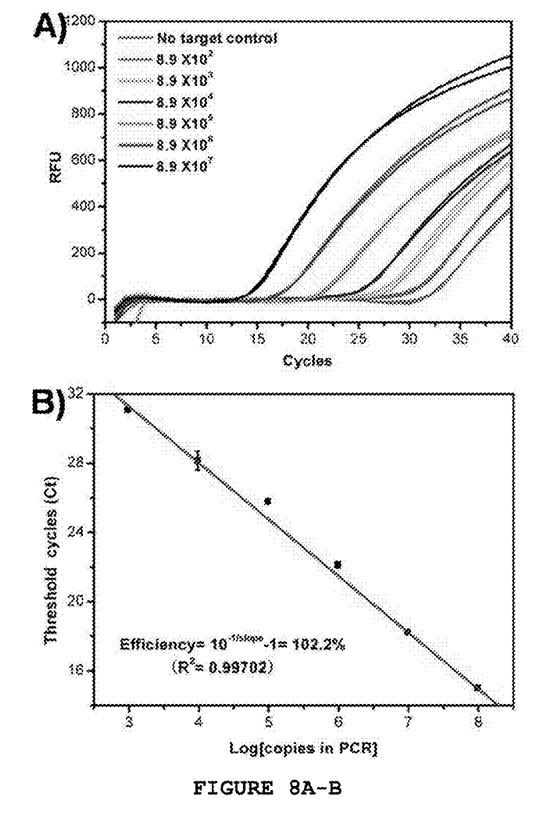

A CE-LIF (laser induced fluorescence) method was applied to demonstrate the M2 chip-based selective binding and extraction of small RNAs. A 63 nt oligo (mixed base A, C, G), physically mimicking pre-miRNAs but with less susceptibility to RNase degradation, was used as a size marker. Experiments show that the CE-LIF method can detect as low as 0.25 nM of 63 nt oligo (FIG. 7, ESI†). With this sensitivity, CE-LIF method was used to analyze the isolated large DNAs/RNAs (eluted from SMP-1) and small RNAs (eluted from SMP-2). CE conditions were the same as in FIG. 7, except that separation field for RNA ladder was 364 V/cm. In these experiments, mir-191 (108 copies) was spiked into 0.7 uL of 63 nt oligo (1 μM) or 0.1-2 kb RNA ladder (80 ng/μL), and the CE results can be seen in FIG. 4A and FIG. 4B, respectively. FIG. 4C was the results of real-time RT-qPCR from eluted and collected miRNAs. These results show that after M2 chip-based purification process, large DNA/RNA molecules can only be detected in recovered fractions eluted from SMP-1, and are undetectable from recovered fractions eluted from SMP-2. Re-isolated mir-191 in different samples can be amplified by RT-qPCR and show similar cycle threshold (Ct) values. For SMP-1/sample mixing procedure, on-chip mixing and in-tube vortexing shows no significant difference. These experiments demonstrate the capability of the presented M2 chip-based protocol for miRNA selective binding and high-purity extraction from 63 nt RNA molecules, which may inhibit expression analysis of miRNA molecules.

Figure 5A:
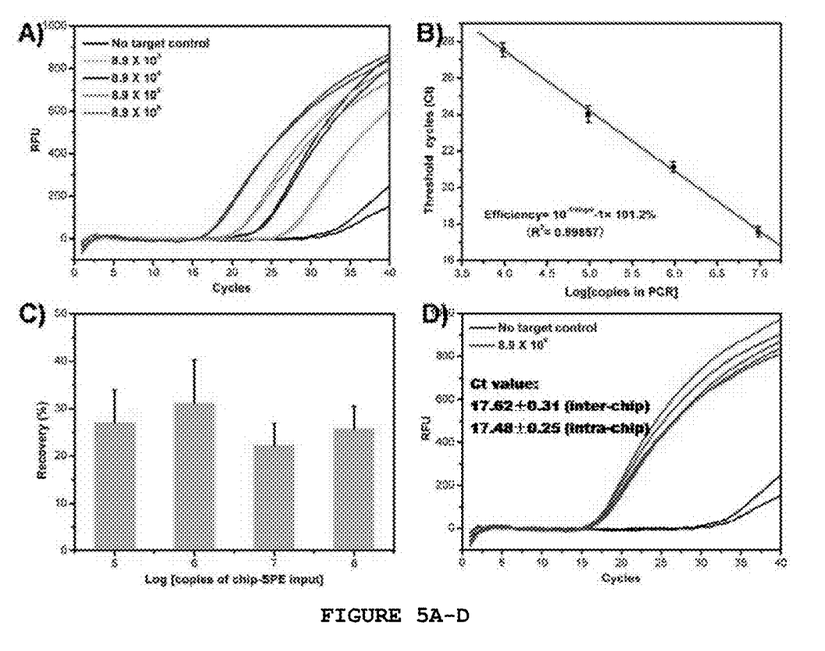

Performance for miRNA purification. The performance of the M2 chip platform was demonstrated in FIG. 5. In these experiments, hsa-mir-191 was spiked into 2.5 μL of E. coli cell lysate matrix with copy numbers of 105, 106, 107, 108, and the eluents were amplified by using TaqMan microRNA real-time RT-qPCR method. Pipette collected eluents (2.5 μL) were added to 5 μL of RT pre-mix to perform RT reaction; then 0.67 μL of RT product was mixed with 9.33 μL of PCR pre-mix to run real-time qPCR. Data represent three independent experiments and error bars represent standard deviations. FIG. 5A is the representative amplification profiles. Amplification efficiency (101.2%, $R^2>0.998$) was calculated from the copy numbers in PCR and the Ct values (FIG. 5B). Recovery (20%-30%) of different miRNA input (FIG. 5C) was determined according to a calibration curve. Reproducibility of intership-(Ct=17.62±0.31, n=4) and intrachip-(Ct=17.48±0.25, n=4) miRNA SPE was measured by using $10^8$ copies of mir-191 input (FIG. 5D). The results demonstrate efficient and reproducible purification of high-quality miRNAs from cell lysate matrix using the M2 chip platform. Reliable performance and linearity in downstream RT-qPCR of the purified miRNA can be obtained.

MicroRNA Analysis from Cell Lysate.

Figure 6A:
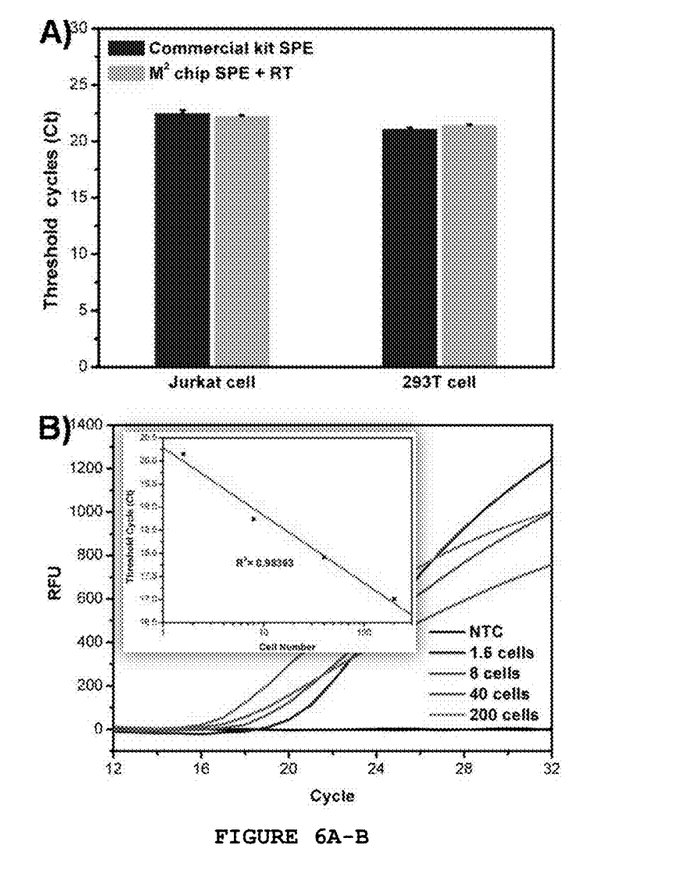
Figure 9:
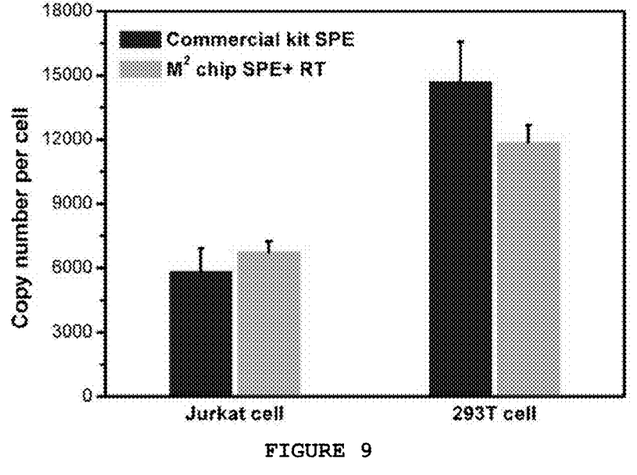
FIG. 9 shows expression levels of hsa-mir-191 in two cell lines. Data was from FIG. 6A. The results demonstrate a higher expression level of hsa-mir-191 in 293T cell line than that in Jurkat cell line.

The performance of the M2 chip-based SPE and RT reaction of miRNA from cell lysate samples were tested and compared with a commercial kit. In these experiments, around $10^6$ cells were resuspended in lysis/binding (L3) buffer, mixed well and then diluted to a concentration of 80 cell/μL using L3 buffer. For M2 chip-based method, 2.5 μL of cell lysate was loaded and finally eluted into 0.915 μL of RNase-free water for on-chip RT reaction. Using commercial spin columns, 100 μL of cell lysate was required for sample load and finally eluted into 100 μL of RNase-free water, from which 0.915 μL of eluent was injected into the control well of the M2 chip for RT reaction. The control wells can be utilized to perform negative and/or positive controls, or to obtain a calibration curve by running the standard serial dilutions. After addition of 0.585 μL of RT pre-mix to the eluted miRNAs, on-line RT reaction was run and the RT products were collected by pipette to perform real-time qPCR (7.5 μL reaction). FIG. 6A shows very close Ct values between chip-based and kit-based method from lysates of two cell lines, Jurkat and 293T; each data was repeated at least three times. The results indicated the comparable performance of the M2 chip and the commercial kit for purification of miRNAs from cell lysate samples, but the M2 chip-based method required only a small fraction (1:40) of the sample volume used by spin column procedure. Furthermore, it was feasible to integrate SPE and RT reaction on the M2 chip, enabling on-line transcription of unstable miRNA to relatively stable cDNA to minimize experimental loss, bias, or variations for downstream applications. The results also demonstrate a higher expression level of hsa-mir-191 in 293T cell line than that in Jurkat cell line (FIG. 9).

Sensitivity of cell numbers was measured by purifying a serial dilutions of 293T cell lysate (200, 40, 8, 1.6 cells input) via M2 chip and performing on-line RT reaction and off-line real-time qPCR detection. Amplification profiles and the calibration curve ($R^2>0.98$) can be seen in FIG. 6B, which indicates a single cell level of mir-191 detection from 293T cell lysate.

Figure 10A:
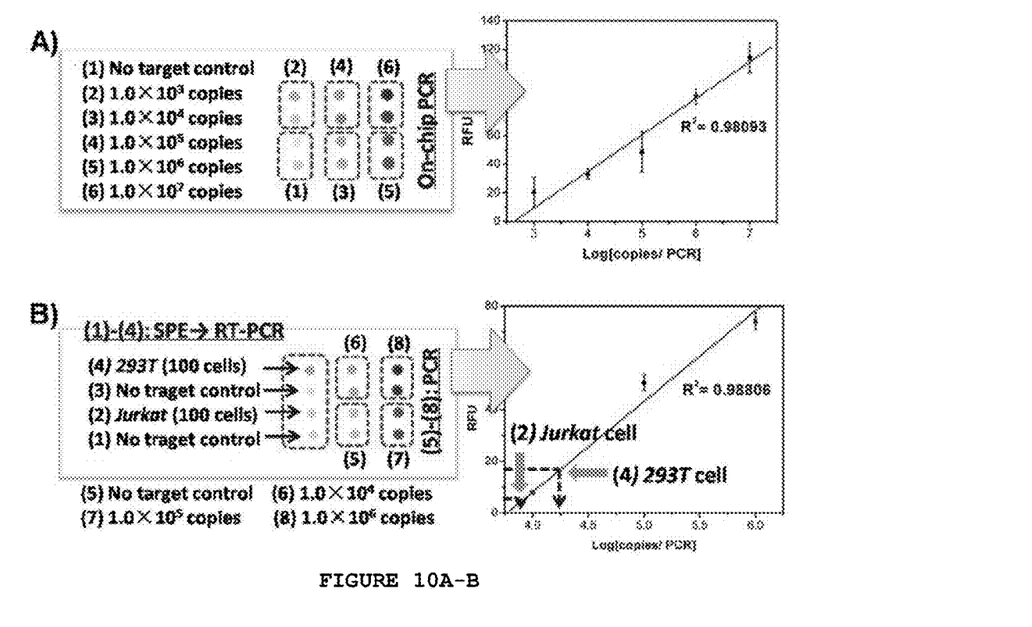

To improve the sample processing throughput of the current M2 chip platform, there are several options available: using the same chip size with a more compact design, using a larger chip size with the same design scheme, or operating several chips simultaneously on a multichannel syringe pump. The last one may provide more flexibility in different applications. For further performance improvement of the M2 chip, the possibility of integrating PCR (FIG. 10(A)) and SPE+ RT-PCR (FIG. 10(B)) was tested on the M2 chip platform for miRNA analysis. Although the preliminary results seem not comparable with the real-time qPCR results, which may be attributed to the inefficient temperature control of M2 chip as well as the PCR product end-point detection method, further developments with micro temperature controller and real-time fluorescence detector are expected to enable the M2 chip platform as a fully integrated microdevice for parallel miRNA purification, amplification and detection/quantitation.

A number of embodiments have been described. Nevertheless, it will be understood that various modifications may be made without departing from the spirit and scope of the description. Accordingly, other embodiments are within the scope of the following claims.

What is claimed is:

1. A valveless microfluidic system comprising
   a substrate;
   a plurality of wells located on the substrate;
   at least one channel fluidly connecting each of the wells from an inlet to an outlet,
   each well comprising a reagent or buffer and the channel comprising a liquid that is immiscible with the reagent or buffer;
   wherein each of the plurality of wells confines an aqueous droplet comprising the reagent or buffer that is surrounded by the immiscible liquid, wherein the aqueous droplet does not evaporate or disperse into the at least one channel; and
   wherein a first well of the plurality of wells comprises a magnetic bead comprising an analyte binding molecule.

2. The microfluidic system of claim 1, wherein the fluidic system comprises a plurality of channels and a plurality of wells fluidly connected with each channel.

3. The microfluidic system of claim 1, wherein the analyte binding molecule comprises an oligonucleotide, peptide, polypeptide, antibody or nanoparticle.

4. The microfluidic system of claim 1, further comprising a magnet for moving the magnetic beads through the at least one channel, the magnet positioned relative to the substrate to provide a magnetic field that manipulates the magnetic bead.

5. The microfluidic system of claim 4, further comprising a computer controller for moving the magnet relative to the substrate.

6. The microfluidic system of claim 1, wherein each well comprises an aqueous droplet and the at least one channel comprises an oil.

7. The microfluidic system of claim 1, wherein the buffer is selected from the group consisting of a binding buffer, a purification buffer, a wash buffer, a lyse buffer, an elution buffer or any combination of the foregoing.

8. The microfluidic system of claim 1, wherein the plurality of wells are each independently selected from the group consisting of a sample well, a wash well, a trap well, a collection well, an elution well and a control well.

9. The microfluidic system of claim 8, wherein the at least one channel fluidly connecting each of the plurality of wells comprises varying dimensions between types of the plurality of wells.

10. The microfluidic system of claim 9, wherein the at least one channel between a sample well and a wash well is wider than the at least one channel between the wash well and the elution well.

11. A kit comprising the microfluidic system of claim 1.

12. A method of purifying an analyte comprising passing a sample comprising an analyte through the at least one channel and the plurality of wells from the inlet to the outlet of the microfluidic system of claim 1, wherein one or more wells of the plurality of wells comprises a purification buffer, lyse buffer or a combination thereof and isolating the analyte from the outlet.

13. The method of claim 12, wherein a magnetic bead comprising the analyte binding molecule is moved through the at least one channel by movement of a magnet adjacent to the microfluidic device.

14. The method of claim 12, wherein the method purifies an oligonucleotide.

15. The method of claim 12, wherein the method amplifies and purifies an oligonucleotide.

\* \* \* \* \*